United States Patent
Schär et al.

(10) Patent No.: US 6,176,881 B1
(45) Date of Patent: Jan. 23, 2001

(54) TELESCOPIC VERTEBRAL PROSTHESIS

(75) Inventors: Manuel Schär, Muttenz; Alex Hatebur, Basel; Fridolin Schläpfer, Glarus, all of (CH)

(73) Assignee: Synthes, Paoli, PA (US)

( * ) Notice: Under 35 U.S.C. 154(b), the term of this patent shall be extended for 0 days.

(21) Appl. No.: 09/402,995

(22) PCT Filed: Apr. 15, 1997

(86) PCT No.: PCT/CH97/00151
§ 371 Date: Oct. 15, 1999
§ 102(e) Date: Oct. 15, 1999

(87) PCT Pub. No.: WO98/46173
PCT Pub. Date: Oct. 22, 1998

(51) Int. Cl.[7] ............................................. A61F 2/44
(52) U.S. Cl. ............................ 623/17.11; 623/17.13; 623/17.15; 606/71; 606/73
(58) Field of Search ..................... 623/17.11, 17.13, 623/17.15, 17.16, 16.11, 18.11; 606/61, 73, 74, 75

(56) References Cited

U.S. PATENT DOCUMENTS

| | | | |
|---|---|---|---|
| 4,554,914 | 11/1985 | Kapp et al. ..................... | 128/92 C |
| 5,236,460 | * 8/1993 | Barber .............................. | 623/17.11 |
| 5,489,308 | * 2/1996 | Kuslich et al. ................... | 623/17.11 |
| 5,702,453 | * 12/1997 | Rabbe et al. ..................... | 623/17.11 |
| 5,723,013 | * 3/1998 | Jeanson et al. .................. | 623/17.11 |
| 5,989,290 | * 11/1999 | Biedermann et al. ............ | 623/17.11 |
| 6,015,436 | * 1/2000 | Schonhoffer ..................... | 623/17.11 |

FOREIGN PATENT DOCUMENTS

| | | |
|---|---|---|
| 2088066 | 1/1992 | (CA) . |
| 37 41 487 A1 | 6/1989 | (DE) . |
| 40 12 622 C1 | 7/1991 | (DE) . |
| 195 00 170 C1 | 2/1996 | (DE) . |
| 196 04 246 A1 | 8/1996 | (DE) . |
| 0 490 159 A1 | 6/1992 | (EP) . |
| WO 92/01428 | 2/1992 | (WO) . |
| WO 94/18913 | 9/1994 | (WO) . |

* cited by examiner

*Primary Examiner*—Pedro Philogene
(74) *Attorney, Agent, or Firm*—Pennie & Edmonds LLP

(57) ABSTRACT

The invention relates to a device for replacing vertebral bones. The device includes an interior hollow body and an exterior hollow body. These hollow bodies can slide into each other coaxially along a central axis and can be moved in relation to one another in the direction of the central axis. The interior hollow body is provided with a catch mechanism on its outer surface. The exterior hollow body includes a hole or bore extending along the central axis. The exterior hollow body also includes at least one elastic element that projects into the bore at its top end. This reduces the diameter of the bore so that the elastic element latches onto the catch mechanism of the interior hollow body, thereby fixing the length of the device in such a way that it is resistant to compression.

18 Claims, 2 Drawing Sheets

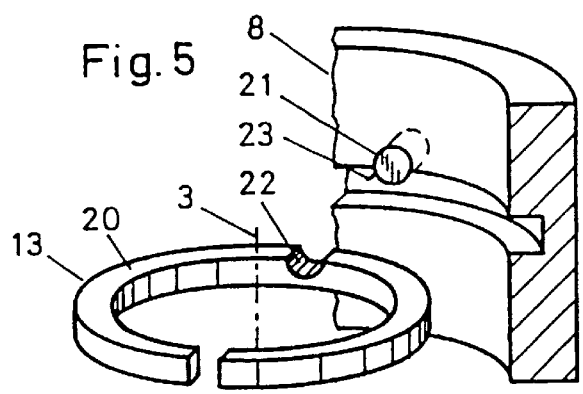
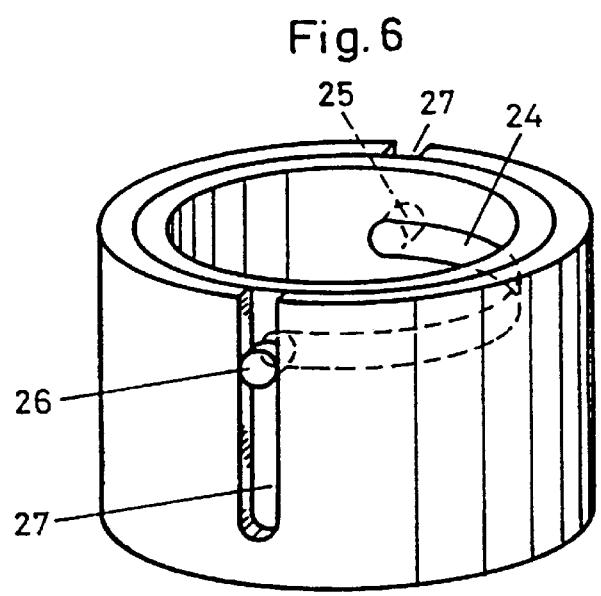
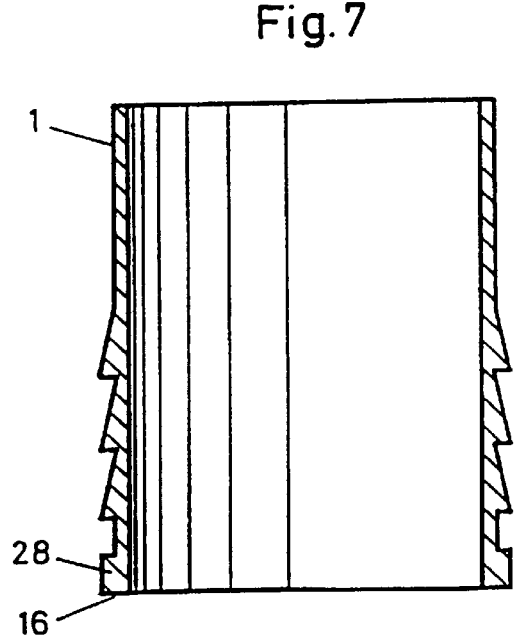

TELESCOPIC VERTEBRAL PROSTHESIS

FIELD OF THE INVENTION

The present invention concerns a device for replacing vertebrae from the human spinal column.

BACKGROUND OF THE INVENTION

If a vertebra becomes diseased or suffers a defect, it must be removed from the spinal column. Some spacer implants for replacement of missing vertebrae are known from the related art. The implant includes mutually displaceable parts which permit an adjustment of the length of the implant by means of catch mechanisms, among other things, and two special end plates which serve to anchor the implant in the adjacent intact vertebrae. Such vertebral prostheses or implants are known, for example, from Austrian Patent R 24426 RASHEED or German Patent No. 196 04 246 A1 JEANSON.

The disadvantage of the these and similar vertebral prostheses is that the two mutually displaceable parts are not closed hollow cylinders and therefore the entire vertebral prosthesis has a low rigidity.

The object of this invention is to obtain the biomechanical and physiological properties of the spinal column despite the removal of a vertebra by using a stable vertebral prosthesis that is adjustable in length. Additionally, ease of handling of the vertebral implant in the course of the surgery is also very important.

This invention achieves this object with a device having the features of claim 1.

SUMMARY OF THE INVENTION

The present invention relates to a vertebral bone prosthetic device having a rigid interior hollow body provided with an outer surface and a catch mechanism thereon. An exterior hollow body has a hole bored therein along a central axis, and is configured and dimensioned to be slidably received by the interior hollow body along the central axis. At least one elastic element projects into the hole thereby reducing the diameter of the bore, and the at least one elastic element engages the catch mechanism for securing the interior hollow body to the exterior hollow body.

In a preferred embodiment of the invention, the vertebral bone prosthetic device has a groove that defines a contact surface, with the groove and the spring having mating conical tapers. At least one hollow body is angled with respect to the central axis, and at least one hollow body has a non-circular cross section.

In another preferred embodiment of the vertebral bone prosthetic device, each catch mechanism includes at least one face defined by a face plane and the at least one face is oriented transverse to a top plane defined by a top end of the interior hollow body. The spring has a pressure-loaded side, with the catch mechanism disposed on the pressure-loaded side.

One embodiment of the device according to this invention includes two telescoping hollow cylinders. The interior hollow cylinder is provided with a catch mechanism on its outer periphery. The exterior hollow cylinder has at least one elastic element which latches into the catch mechanism of the interior hollow cylinder and fixes the length of the device. With the catch mechanism and the latchable elastic element, the device according to this invention can be lengthened and adjusted during surgery.

Another embodiment of the device according to this invention includes two coaxially arranged hollow bodies that are displaceable along said axis relative to one another, a spring mounted in a groove provided in the exterior hollow body and end plates that serve to anchor the device in the adjacent vertebrae. The interior hollow body is provided with a catch mechanism on its outer surface. On its inner surface, the spring has a catch mechanism which fixes the interior hollow body in the axial direction when it latches into the catch mechanism on said interior hollow body. The spring can also be spread from the outside by using an auxiliary instrument through an opening in the exterior hollow body thereby allowing controlled in situ compression. An embodiment with three hollow bodies that can slide into each other is also possible, with the outer and interior hollow cylindrical surfaces each being designed as in the two-part variant described above.

The advantages achieved through this variant of the invention are to be seen essentially as the fact that a spring with a catch mechanism is built into the device according to this invention to fix the length of the implant. The overall height of the implant can thus be reduced, and when the clearance is small, it can be inserted between adjacent vertebrae, which thus permits the use of this prosthesis even in the vicinity of the cervical vertebrae. By spreading the spring, the vertebral prosthesis according to this invention can be compressed again and removed. In addition, the two hollow cylinders may have relatively thick walls and thus may form a very stable prosthesis.

BRIEF DESCRIPTION OF THE DRAWINGS

The present invention and further refinements of this invention are explained in greater detail below on the basis of the partially schematic diagrams of several embodiments, which show:

FIG. 5: a perspective view of the ring-shaped spring 13 with a detail from the exterior hollow body according to one embodiment of the device according to this invention;

FIG. 6: a perspective detail of the two hollow bodies 1, 2 and an elastic strap 24 according to one embodiment of the device according to this invention; and FIG. 7: another embodiment of the interior hollow body 1 of the device according to this invention.

DETAILED DESCRIPTION OF THE PREFERRED EMBODIMENTS

Figure 1:
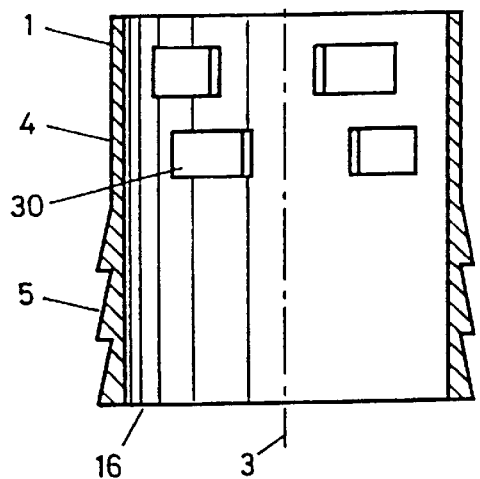
FIG. 1: a longitudinal section through the interior hollow body 1 of the device according to this invention.

FIG. 1 shows the interior hollow body according to an embodiment of the device according to this invention. The catch mechanism 5 on the outer surface is applied to only a part of the length of the interior hollow body. Depending on the design of the device according to this invention, the part of the interior hollow body 1 not provided with the catch mechanism 5 is equipped with radial passages 30.

Figure 2:
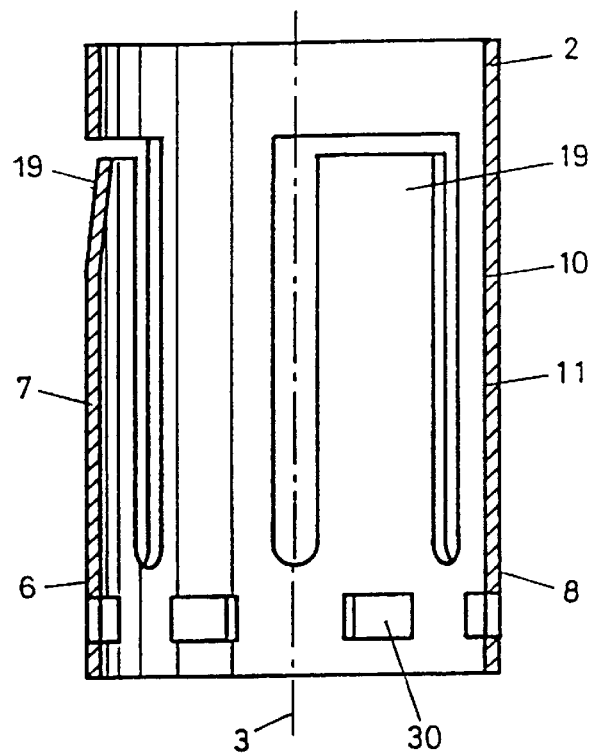
FIG. 2: a longitudinal section through the exterior hollow body 2 of a variant of the device according to this invention.

The exterior hollow cylinder 2 shown in FIG. 2 corresponds to an embodiment of the device according to this invention having multiple tongues 19 as elastic element 7; these tongues are cut out of the wall 6 of the exterior hollow cylinder 2 and bent toward the central axis 3. Depending on the embodiment of the device according to this invention, the exterior hollow cylinder 2 is equipped with radial passages 30.

Figure 3:
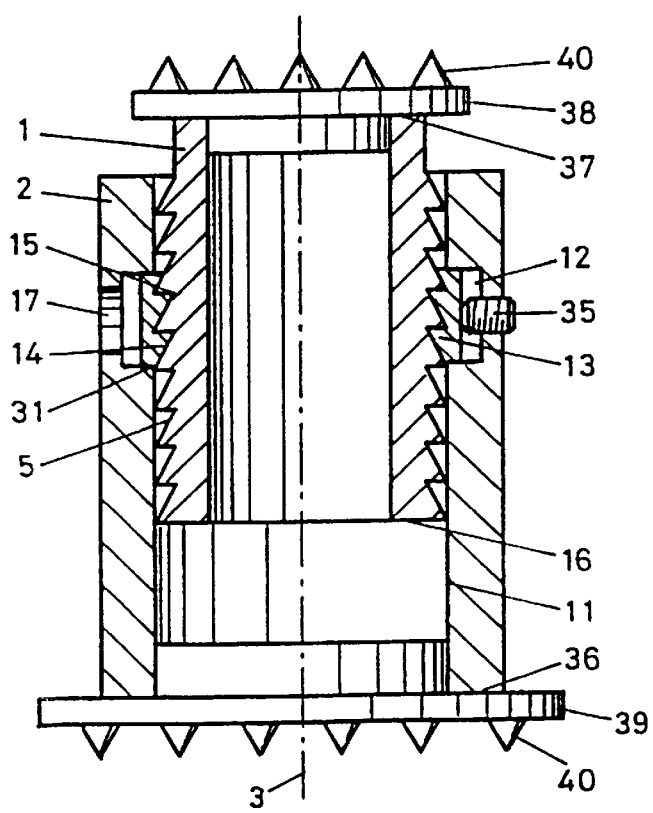
FIG. 3: a longitudinal section through another embodiment of the device according to this invention.

The variant of the device according to the present invention shown in FIG. 3 illustrates the exterior hollow body 2, which is provided with on the inside, surface 11 coaxially with central axis 3, a cylindrical bore 10, a cylindrical groove 12 and an opening 17 extending from this groove 12 to the outer surface of the exterior hollow body 2. The interior hollow body 1, which is provided with a catch mechanism 5 on its outer surface, 4 is arranged so it can slide in the exterior hollow body 2 and can be displaced relative to it along the central axis 3. A spring 13, which is provided on the inside with a catch mechanism 14 with a form fit with the catch mechanism 5 of interior hollow body 1, is inserted into the groove 12. If the spring 13 is spread with an auxiliary means which can be inserted into the gap 18 of spring 13 through the opening 17 in the exterior hollow element 2, the interior hollow body 1 can be displaced in both directions relative to the exterior.

Another variant of the device according to this invention as shown in FIG. 3 is equipped with a locking screw 35 passing radially through the exterior hollow body 2 in the area of groove 12 to block the two hollow bodies 1, 2 in the direction of the central axis 3.

FIG. 3 also shows variants of the device according to the present invention; they are equipped with end plates 38, 39, which may have mandrels 40 on the bone side, on both free ends 36, 37 of the hollow bodies 1, 2.

Figure 4:
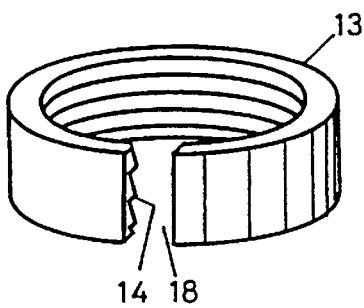
FIG. 4: a perspective view of the ring-shaped spring 13 according to one embodiment of the device according to this invention.

The ring-shaped spring 13 of the device according to the present invention as illustrated in FIG. 3 is shown in FIG. 4. The spring 13 is opened at the periphery through a gap 18. A catch mechanism 14 which can be latched into the catch mechanism 5 on the outer periphery of interior hollow body 1 is attached to the inner surface of the ring-shaped spring 13.

FIG. 5 shows another embodiment of the version of the device according to this invention as shown in FIG. 3. A pin 21 is inserted into an opening 23 passing radially through the exterior hollow body 2, engaging in a notch 22 on the top end face 20 of the spring 13, thus preventing the spring 13 from rotating about the central axis 3.

FIG. 6 shows another embodiment of the device according to the present invention. An elastic strap 24 with free ends 25, 26 that are bent outward and can be latched into longitudinal slits 27 on the exterior hollow body 2 secures the two hollow bodies 1, 2 to prevent rotation.

In another embodiment shown in FIG. 7 of the version of the device according to the present invention shown in FIG. 3, the interior hollow body 1 is provided with a shoulder 28 on its lower end 16, the outside diameter of said shoulder being greater than the inside diameter of the unextended spring 13. The shoulder 28 on the bottom end 16 prevents the interior hollow body 1 from sliding upward along spring 13, thereby slipping out of the exterior hollow body 2.

What is claimed is:

1. A vertebral bone prosthetic device comprising:
   a rigid interior hollow body provided with an outer surface and a catch mechanism thereon;
   an exterior hollow body with a hole therein extending along a central axis, with the exterior hollow body being configured and dimensioned to be slidably received by the interior hollow body along the central axis; and
   an at least one elastic element projecting into the hole to engage the catch mechanism for securing the interior hollow body to the exterior hollow body.

2. The vertebral bone prosthetic device of claim 1 wherein at least one hollow body is a hollow cylinder.

3. The vertebral bone prosthetic device of claim 1 wherein the at least one elastic element is a tongue formed in a wall of the exterior hollow body.

4. The vertebral bone prosthetic device of claim 1, wherein the exterior hollow body includes longitudinal slits and the device further comprises an elastic strap having bent free ends latchable in the longitudinal slits to prevent twisting of the exterior and interior hollow bodies.

5. The vertebral bone prosthetic device of claim 1 further comprising a ring-shaped spring having inside periphery with a spring catch mechanism disposed thereon and a gap, wherein the spring is mounted in a groove formed in the inside surface of the exterior hollow body and wherein the spring catch mechanism engages the catch mechanism of the interior hollow body.

6. The vertebral bone prosthetic device of claim 5 further comprising auxiliary means insertable through a hole in the exterior hollow body, wherein the auxiliary means engages the gap of the spring thereby unlatching the spring catch mechanism from the catch mechanism of the interior hollow body.

7. The vertebral bone prosthetic device of claim 5, wherein the spring includes an end face and a notch thereon.

8. The vertebral bone prosthetic device of claim 7 further comprising a pin which is insertable through a hole in the exterior hollow body for engaging the notch in the spring to secure the spring and prevent its rotation about the central axis.

9. The vertebral bone prosthetic device of claim 5, wherein the interior hollow body is provided with a shoulder on its lower end, the outside diameter of the shoulder being greater than the inside diameter of the spring, thereby preventing relative sliding movement between the interior hollow body and the exterior hollow body.

10. The vertebral bone prosthetic device of claim 5, wherein the groove defines a contact surface, the groove and the spring having mating conical tapers.

11. The vertebral bone prosthetic device of claim 5, wherein each catch mechanism includes at least one face defined by a face plane and is oriented transverse to a top plane defined by a top end of the interior hollow body.

12. The vertebral bone prosthetic device of claim 11, wherein the spring has a pressure-loaded side, and the catch mechanism is disposed on the pressure-loaded side.

13. The vertebral bone prosthetic device of claim 1, wherein each hollow body has at least one through hole formed in a wall of the hollow body.

14. The vertebral bone prosthetic device of claim 1, wherein at least one hollow body is angled with respect to the central axis.

15. The vertebral bone prosthetic device of claim 1, wherein at least one hollow body has a non-circular cross section.

16. The vertebral bone prosthetic device of claim 1, wherein end plates are mounted on opposing ends of the hollow bodies.

17. The vertebral bone prosthetic device of claim 16, wherein each end plate has a bone side with mandrels mounted thereon.

18. The vertebral bone prosthetic device of claim 1, further comprising a locking screw which is screwed into the exterior hollow body.

* * * * *